United States Patent [19]

Nagai et al.

[11] Patent Number: 5,723,133
[45] Date of Patent: Mar. 3, 1998

[54] COSMETICS CONTAINING GUANIDINE DERIVATIVES

[75] Inventors: Minoru Nagai; Hiromitsu Kawada; Mayumi Tsuchiya; Seiji Yamasaki; Akira Yamamuro; Toshiya Ono, all of Tokyo, Japan

[73] Assignee: Kao Corporation, Tokyo, Japan

[21] Appl. No.: 507,077

[22] Filed: Jul. 26, 1995

[30] Foreign Application Priority Data

Jul. 26, 1994 [JP] Japan ..................... 6-173043
Sep. 22, 1994 [JP] Japan ..................... 6-228023

[51] Int. Cl.$^6$ ..................... A61K 7/48
[52] U.S. Cl. ..................... 424/401; 514/844; 514/846; 514/944; 548/532; 562/11; 562/104; 562/512; 564/237; 564/240
[58] Field of Search ..................... 424/401; 564/237, 564/240; 562/11, 104, 512; 548/532; 514/844, 846, 944

[56] References Cited

FOREIGN PATENT DOCUMENTS 2103605  2/1983  United Kingdom .

*Primary Examiner*—Jyothsan Venkat
*Attorney, Agent, or Firm*—Oblon, Spivak, McClelland, Maier & Neustad, P.C.

[57] ABSTRACT

A guanidine derivative represented by formula (1), (2), (3) or its acid addition salt and a production process thereof

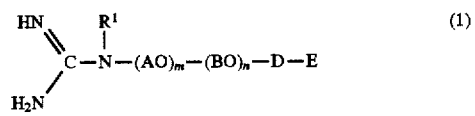

(1)

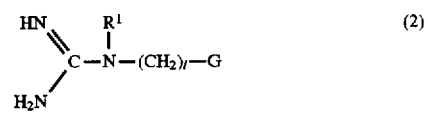

(2)

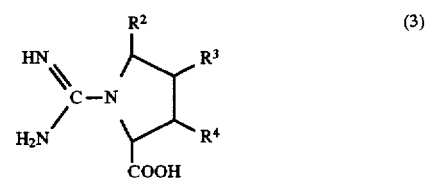

(3)

wherein each of A and B is a $C_2$–$C_8$ alkylene, D is a single bond, —CO— or a $C_1$–$C_5$ alkylene, E is H, a lower alkyl or the like, m is 1 to 6, n is 0 to 6 and $R^1$ is H, a lower alkyl or the like, l is 1 to 10 and G is H, —OH or the like and a skin cosmetic containing the same. It can exert excellent keratin layer softening effect continuously for a long period of time.

4 Claims, No Drawings

COSMETICS CONTAINING GUANIDINE DERIVATIVES

BACKGROUND OF THE INVENTION

1. Field of the Invention

This invention relates to cosmetics which have a keratin layer softening effect and which provide a good feeling when used, to guanidine derivatives including acid addition salts thereof which have a moisturizing effect, a keratin softening effect, etc. and are useful as components of cosmetic formulations and to a process for the production thereof.

2. Discussion of the Background

The keratin layer, the outermost layer of the skin, becomes dry and rough during exposure to low temperature, low moisture, etc., conditions (e.g., in the winter season) or when contacted with detergents or solvents in excess amounts. It is thought that such changes in the skin occur when a hygroscopic water soluble component, called NMF (natural moisturizing factor), in the keratin layer is lost causing a reduction in the water content of and in the softness of the keratin layer. As a consequence, conventional cosmetics for use in softening the skin are blended with various types of moisturizing agents including natural moisturizing components such as organic acids and amino acids, for the purpose of providing the keratin layer with a large quantity of moisture for a prolonged period of time.

An example of such skin softening cosmetics are those in which an α-hydroxy acid having a keratin layer softening function is blended as an organic acid as in JP-A-55-19291 (the term "JP-A" as used herein means an "unexamined published Japanese patent application"). However, α-hydroxy acids have a disadvantage in that their effects are transient and can be obtained only within a low pH range (pH 2 to 4) which inhibits normal skin physiology.

In order to resolve such a problem, some cosmetics are adjusted to a neutral pH range by supplementing them with strong alkalis such as sodium hydroxide, potassium hydroxide and the like or amines such as triethanolamine and the like. These strong alkalis, however have a disadvantage in that the quality of the resulting cosmetics cannot be maintained at a constant level, because these alkalis spoil the stability of the cosmetics when blended in a large amount, and it is difficult to accommodate the pH range of the skin. Amines, on the other hand, are not desirable from a safety point of view because of the possibility to cause allergic reaction.

In order to resolve such problems caused by the blending of α-hydroxy acids, cosmetics in which α-hydroxy acids are used in combination with basic amino acids have been proposed for example in JP-B-3-30556 (the term "JP-B" as used herein means an "examined Japanese patent publication"), but their skin softening effects are not sufficient.

In addition, cosmetics blended with amino acids and their derivatives have been proposed with the aim of obtaining skin softening through improvement of the moisturizing effect, such as those in which the hydrolysate of coix seed and the like are blended (for example, JP-B-58-8007) and in which various types of peptides are blended (for example, JP-A-48-23944, JP-A-62-99315 and JP-A-2-178207). The skin softening effect of these amino acids and peptide compositions, however, are not sufficient.

OBJECTS OF THE INVENTION

An object of the present invention is to overcome the aforementioned problems involved in the prior art and provide skin cosmetics which can soften the keratin layer without spoiling its normal skin physiology and give a proper feeling when used.

SUMMARY OF THE INVENTION

In view of the above, the present inventors have discovered that the use of a guanidine derivative having a specified structure and acid addition salts thereof provide cosmetics having excellent keratin layer softening effects which are superior to conventional materials in which basic amino acids are used alone or in combination with dicarboxylic acids. The present invention has been accomplished on the basis of this finding.

Thus, according to the present invention, there is provided a guanidine derivative represented by formula (1), (2) or (3)

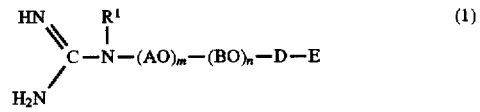

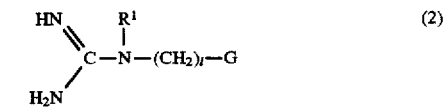

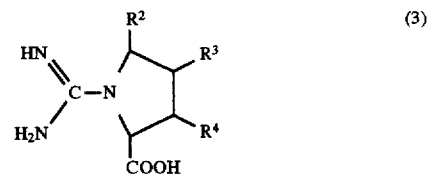

wherein A and B may be the same or different from each other and each represents an alkylene group having 2 to 8 carbon atoms, D represents a single bond, —CO— or an alkylene group having 1 to 6 carbon atoms which may have a substituent group, E represents a hydrogen atom, a lower alkyl group, an aralkyl group or an aryl group which may have a substituent group, m is an integer of 1 to 6, n is an integer of 0 to 6 and $R^1$ represents a hydrogen atom, a lower alkyl group or —(AO)$_m$—(BO)$_n$—D—E, with the provisos that —(AO)$_m$—(BO)$_n$—D—E is not a hydroxyethyl group when $R^1$ is a methyl group, that $R^1$ is not hydrogen when A is a straight chain alkylene group, m=1 and n=0, that —(AO)$_m$—(BO)$_n$—D—E is not hydroxyethyl when $R^1$ is hydrogen, a methyl group or a hydroxyethyl group and that —(AO)$_m$—(BO)$_n$—D—E is not a lower alkoxyethyl group when $R^1$ is hydrogen, in formula (2), l is an integer of 1 to 10, G represents a hydrogen atom, a hydroxyl group, a carboxyl group, a sulfonic acid group or a phosphoric acid group and $R^1$ is as defined immediately above, and, in formula (3), one of $R^2$, $R^3$ and $R^4$ is a hydroxyl group and others are hydrogen atoms. Acid addition salts of Formula (1), (2) or (3) and a process for the production of compounds of Formula (1), (2) or (3) are also part of the invention.

DETAILED DESCRIPTION OF THE INVENTION

The invention guanidine derivative and an acid addition salts thereof are compounds represented by the aforementioned formula (1), (2) or (3). In the formula (1), the alkylene group having 2 to 8 carbon atoms represented by A and B may be either a straight-chain or a branched-chain group, which include ethylene, trimethylene, tetramethylene, pentamethylene, hexamethylene, propylene and like groups, of which those having 2 to 6 carbon atoms are preferred, more preferred are those having 2 to 4 carbon atoms such as ethylene, trimethylene and propylene groups.

The alkylene group having 1 to 6 carbon atoms represented by D may be either a straight-chain or a branched-chain group, which include methylene, ethylene, trimethylene, tetramethylene, pentamethylene, hexamethylene, propylene and like groups.

Examples of the lower alkyl group represented by E or $R^1$ include straight- or branched-chain alkyl groups having 1 to 5 carbon atoms, such as methyl, ethyl, n-propyl, isopropyl, n-butyl, sec-butyl, tert-butyl, pentyl and like groups, of which methyl is particularly preferred.

Examples of the aralkyl group represented by E include those which have 7 to 12 carbon atoms, such as benzyl, phenetyl, naphthylmethyl and like groups.

Examples of the aryl group represented by E include phenyl, naphthyl and like groups, and their substituent groups include amino which may be substituted with a methyl or like lower alkyl group; nitro; cyano; hydroxyl; a carboxylic acid residue which may form an ester with a lower alkyl group, a lower alkyl halide or an aralkyl group; carbamoyl; a halogen atom such as fluorine, chlorine, bromine, iodine or the like; a lower alkyl group such as methyl, ethyl, propyl, isopropyl or the like; and a lower alkoxy group such as methoxy, ethoxy or the like.

In formulae (1), (2) and (3), m is an integer of 1 to 6, preferably 1 to 4, and n is an integer of 0 to 6, preferably 0 to 4.

In the formula (2), $R^1$ is as defined above, 1 is an integer of 1 to 10, preferably 1 to 5, and G is preferably a hydroxyl group, a carboxyl group or a phosphoric group.

In formula (3), a compound wherein $R^3$ is a hydroxyl group, $R^2$ and $R^4$ are hydrogen atoms is particularly preferred. Steroisomers are existed in compounds represented by formula (3) by an asymmetric carbon atom. These steroisomers are also included in the present invention.

Illustrative examples of guanidine derivatives represented by formula (1), (2) or (3) include 2-hydroxyguanidine, 3-hydroxyguanidine, 2-hydroxypropylguanidine, 4-hydroxybutylguanidine, 5-hydroxypentylguanidine, 6-hydroxyhexylguanidine, 2-(2-hydroxyethoxy)ethylguanidine, 2-[2-(2-hydroxyethoxy)ethoxy]ethylguanidine, 1-(3-hydroxypropyl)-1-methylguanidine, 1-(2-hydroxypropyl)-1-methylguanidine, 1-(4-hydroxybutyl)-1-methylguanidine, 1-(5-hydroxypentyl)-1-methylguanidine, 1-(6-hydroxyhexyl)-1-methylguanidine, 1-[2-(2-hydroxyethoxy)ethyl]-1-methylguanidine, 1-[2-(2-(2-hydroxyethoxy)ethoxy)ethyl]-1-methylguanidine, 1,1-bis(2-hydroxyethyl)guanidine, 1,1-bis(3-hydroxypropyl) guanidine, 1,1-bis(2-hydroxypropyl)guanidine, 1,1-bis(4-hydroxybutyl)guanidine, 1,1-bis(5-hydroxypentyl) guanidine, 1,1-bis(6-hydroxyhexyl)guanidine, 1,1-bis[2-(2-hydroxyethoxy)ethyl]guanidine, 1,1-bis[2-(2-(2-hydroxyethoxy)ethoxy)ethyl]guanidine, (2-methoxyethyl) guanidine, (2-ethoxyethyl)guanidine, (3-methoxypropyl) guanidine, (2-methoxypropyl)guanidine, (4-methoxybutyl) guanidine, (5-methoxypentyl)guanidine, 2-(2-methoxyethoxy)ethylguanidine, [2-(2-(methoxyethoxy) ethoxy)ethyl]guanidine, 1,1-bis(2-methoxyethyl)guanidine, 1,1-bis(2-ethoxyethyl)guanidine, 1,1-bis(3-methoxypropyl) guanidine, 1,1-bis(2-methoxypropyl)guanidine, 1,1-bis(4-methoxybutyl)guanidine, 1,1-bis(5-methoxypentyl) guanidine, 1,1-bis(4-methoxybutyl)guanidine, 1,1-bis(5-methoxypentyl)guanidine, 1,1-bis(6-methoxyhexyl) guanidine, 1,1-bis[2-(2-methoxyethoxy)ethyl]guanidine, 1,1-bis[2-(2-(2-methoxyethoxy)ethoxy)ethyl]guanidine,
1-(2-methoxyethyl)-1-methylguanidine, 1-(2-ethoxyethyl)-1-methylguanidine, 1-(3-methoxypropyl)-1-methylguanidine, 1-(2-methoxypropyl)-1-methylguanidine, 1-(4-methoxybutyl)-1-methylguanidine, 1-(5-methoxypentyl)-1-methylguanidine, 1-(6-methoxyhexyl)-1-methylguanidine, 1-[2-(2-(methoxyethoxy)ethyl-1-methylguanidine, 1-[2-(2-(2-(methoxyethoxy)ethoxy)ethyl] -1-methylguanidine, 2-guanidinoethyl acetate, 3-guanidinopropyl acetate, 2-guanidino-2-propyl acetate, 4-guanidino-1-butyl acetate, 5-guanidino-1-pentyl acetate, 6-guanidino-1-hexyl acetate, 2-(2-guanidinoethoxy)ethyl acetate, 2-[2-(2-guanidinoethoxy)ethoxy]ethyl acetate, 2-(1-methylguanidino)ethyl acetate, 3-(1-methylguanidino) propyl acetate, 2-(1-methylguanidino)-1-methylethyl acetate, 4-(1-methylguanidino)butyl acetate, 5-(1-methylguanidino)pentyl acetate, 6-(1-methylguanidino) pentyl acetate, 2-[2-(1-methylguanidino)ethoxy]ethyl acetate, 2-[2-(2-(1-methylguanidino)ethoxy)ethoxy]ethyl acetate, 2-guanidinoethyl benzoate, 3-guanidinopropyl benzoate, 2-guanidino-2-propyl benzoate, 4-guanidino-1-butyl benzoate, 5-guanidino-1-pentyl benzoate, 6-guanidino-1-hexyl benzoate, 2-(2-guanidinoethoxy)ethyl benzoate, 2-[2-(2-guanidinoethoxy)ethoxy]ethyl benzoate, 2-(1-methylguanidino)ethyl benzoate, 3-(1-methylguanidino)propyl benzoate, 2-(1-methylguanidino)-1-methylethyl benzoate, 4-(1-methylguanidino)butyl benzoate, 5-(1-methylguanidino)pentyl benzoate, 6-(1-methylguanidino)pentyl benzoate, 2-[2-(1-methylguanidino)ethoxy]ethyl benzoate, 2-[2-(2-(1-methylguanidino)ethoxy)ethoxy]ethyl benzoate, 2-guanidinoethyl salicylate, 3-guanidinopropyl salicylate, 2-guanidino-2-propyl salicylate, 4-guanidino-1-butyl salicylate, 5-guanidino-1-pentyl salicylate, 6-guanidino-1-hexyl salicylate, 2-(2-guanidinoethoxy)ethyl salicylate, 2-[2-(2-guanidinoethoxy)ethoxy]ethyl salicylate, 2-(1-methylguanidino)ethyl salicylate, 3-(1-methylguanidino) propyl salicylate, 2-(1-methylguanidino)-1-methylethyl salicylate, 4-(1-methylguanidino)butyl salicylate, 5-(1-methylguanidino)pentyl salicylate, 6-(1-methylguanidino) pentyl salicylate, 2-[2-(1-methylguanidino)ethoxy]ethyl salicylate, 2-[2-(2-(1-methylguanidino)ethoxy)ethoxy]ethyl salicylate, 2-guanidinoethyl m- or p-hydroxybenzoate, 3-guanidinopropyl m-or p-hydroxybenzoate, 2-guanidino-2-propyl m- or p-hydroxybenzoate, hydroxybenzoate, 4-guanidino-1-butyl m- or p-hydroxybenzoate, 5-guanidino-1-pentyl m- or p-hydroxybenzoate, 6-guanidino-1-hexyl m- or p-hydroxybenzoate, 2-(2-guanidinoethoxy)ethyl m- or p-hydroxybenzoate, 2-[2-(2-guanidinoethoxy)ethoxy]ethyl m-or p-hydroxybenzoate, 2-(1-methylguanidino)ethyl m- or p-hydroxybenzoate, 3-(1-methylguanidino)propyl m- or p-hydroxybenzoate, 2-(1-methylguanidino)-1-methylethyl m- or p-hydroxybenzoate, 4-(1-methylguanidino)butyl m- or p-hydroxybenzoate, 5-(1-methylguanidino)pentyl m- or p-hydroxybenzoate, 6-(1-methylguanidino)pentyl m- or p-hydroxybenzoate, 2-[2-(1-methylguanidino)ethoxy]ethyl m- or p-hydroxybenzoate, 2-[2-(2-(1-methylguanidino) ethoxy)ethoxy]ethyl m- or p-hydroxybenzoate, N-(aminoiminomethyl)-trans-4-hydroxy-L-proline and the like.

Of these guanidine derivatives, 2-(2-hydroxyethoxy) ethylguanidine, 5-hydroxypentylguanidine, 3-guanidinopropanoic acid, 2-guanidinoethyl dihydrogen phosphate and N-(aminoiminomethyl)-trans-4-hydroxy-L-proline are particularly preferred.

Either organic or inorganic acids may be used to form acid addition salts of the invention guanidine derivatives of both formulae (1), (2) and (3), which include, for example:

monocarboxylic acids such as formic acid, acetic acid, propionic acid, butylic acid, isobutylic acid, hexanoic acid, heptanoic acid, octanoic acid, nonanoic acid, decanoic acid, lauric acid, myristic acid, palmitic acid, stearic acid, acrylic acid, methacrylic acid, crotonic acid, isocrotonic acid, phenylacetic acid, cinnamic acid, benzoic acid, sorbic acid, nicotinic acid, urocanic acid, pyrrolidonecarboxylic acid and the like; dicarboxylic acids such as oxalic acid, malonic acid, succinic acid, glutaric acid, adipic acid, pimelic acid, cork acid, azelaic acid, sebacic acid, maleic acid, fumaric acid, phthalic acid, terephthalic acid and the like; hydroxy acids such as glycolic acid, lactic acid, malic acid, tartaric acid, citric acid, o-, m- or p-hydroxybenzoic acid and the like; amino acids such as glycine, alanine, β-alanine, valine, leucine, phenylalanine, tyrosine, serine, threonine, methionine, cysteine, cystine, proline, hydroxyproline, pipecolic acid, tryptophan, aspartic acid, asparagine, glutamic acid, glutamine, lysine, histidine, ornithine, arginine, aminobenzoic acid and the like; lower alkylsulfonic acids such as methanesulfonic acid, trifluoromethanesulfonic acid and the like; arylsulfonic acids such as benzenesulfonic acid, p-toluenesulfonic acid and the like; hydrohalogenic acid such as hydrofluoric acid, hydrochloric acid, hydrobromic acid, hydroiodic acid and the like; and inorganic acids such as perchloric acid, sulfuric acid, nitric acid, phosphoric acid, carbonic acid and the like.

The guanidine derivative represented by the formula (1) or acid addition salts thereof can be produced for example by a process represented by the following reaction formula

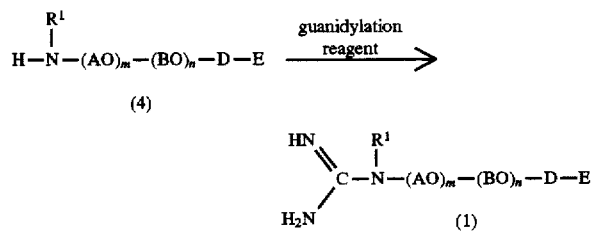

wherein A, B, D, E, m, n and R¹ are as defined in the foregoing.

That is, the guanidine derivative (1) or salts thereof can be obtained by allowing a guanidylation reagent to react with amine derivative (4).

Illustrative examples of the amine derivative (4) which is useful as the starting material include 2-(2-aminoethoxy) ethanol, 2-(2-(2-aminoethoxy)ethoxy)ethanol, 1-amino-2-propanol, 2-(2-N-methylaminoethoxy)ethanol, 2-(2-(2-N-methylaminoethoxy)ethoxy)ethanol, 1-N-methylamino-2-propanol, N,N-bis-(2-hydroxyethoxy)ethylamine, N,N-bis-(2-(2-(2-hydroxyethoxy)ethoxy)ethylamine, N,N-di-(2-hydroxypropyl)amine, 3-N-methylamino-1-propanol, 4-N-methylamino-1-butanol, 5-N-methylamino-1-pentanol, 6-N-methylamino-1-hexanol, di-3-propanolamine, di-4-butanolamine, di-5-pentanolamine, di-6-hexanolaraine, 2-(2-methoxyethoxy)ethylamine, 2-[2-(2-methoxyethoxy) ethoxy]ethylamine, 2-methoxy-1-propylamine, N-methyl-2-(2-methoxyethoxy)ethylamine, N-methyl-2-[2-(2-methoxyethoxy)ethoxy]ethylamine, N-methyl-2-methoxypropylamine, N,N-bis-[2-(2-methoxyethoxy)ethyl] amine, N,N-bis-[2-(2-(2-methoxyethoxy)ethoxy)ethyl] amine, N,N-di-2-methoxypropytlamine, N-methyl-3-methoxypropylamine, N-methyl-4-methoxybutylamine, N-methyl-5-methoxypentylamine, N-methyl-6-methoxyhexylamine, N,N-di-3-methoxypropylamine, N,N-di-4-methoxybutylamine, N,N-di-5-methoxypentylamine, N,N-di-6-methoxyhexylamine and the like.

With regard to the guanidylation reagent, known compounds such as cyanamide, S-alkylisothiourea, O-alkylisourea, aminoiminomethanesulfonic acid, 3,5-dimethyl-1-guanylpyrazole, 1H-pyrazole-1-carboamidine and the like may be used.

When S-alkylisothiourea, O-alkylisourea, 3,5-dimethyl-1-guanylpyrazole or 1H-pyrazole-1-carboamidine is used, the reaction may be effected by 1 to 72 hours of stirring at a temperature of from 0° to 200° C. in the presence of a base such as barium hydroxide, calcium hydroxide, magnesium hydroxide, sodium hydroxide, calcium hydroxide, lithium hydroxide, sodium bicarbonate, sodium carbonate or aqueous ammonia, triethylamine, N,N-dimethylaniline, N,N-dimethylpiperazine, N-methylpiperazine or like tertiary amine, or pyridine. When cyanamide is used, the reaction may be completed by 1 to 72 hours of stirring at a temperature of from 0° to 200° C., or by 1 to 72 hours of stirring at a temperature of from 25° to 160° C. in the presence of an acid illustrated in the foregoing in relation to the acid addition salts of guanidine.

After completion of the reaction, the product may be isolated as an acid addition salt as occasion demands, by adding desired acid in the usual way.

The guanidine derivative represented by the formula (4) or its salt can also be produced in accordance with the aforementioned process.

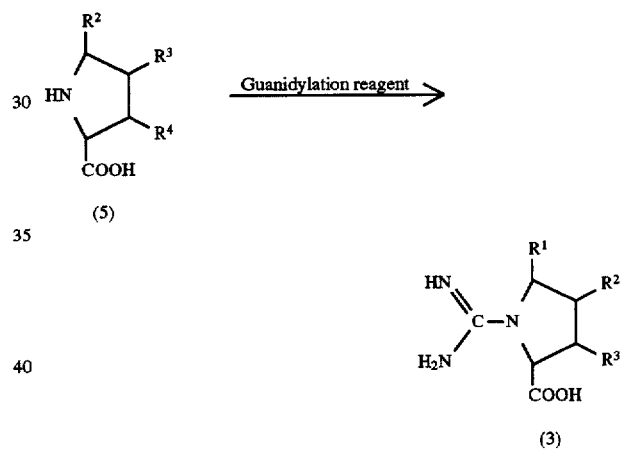

wherein, R², R³ and R⁴ are as defined above.

Guanidine derivative (3) or an acid addition salt is obtained by reacting a guanidylation reagent with prolines (5).

When these guanidine derivatives or salts thereof are blended in a skin cosmetic preparation, they may be used alone or as a mixture of two or more and in an amount of preferably from 0.001 to 50% by weight, more preferably from 0.001 to 30% by weight, most preferably from 0.01 to 20% by weight, including all values and subranges between these several limits in order to improve the skin keratin layer softening effect.

The softening effect of the skin cosmetics of the present invention can be further improved when blended with additional organic acids or inorganic acids such as phosphoric acid, sulfuric acid, hydrochloric acid and the like.

Such organic acids are not particularly limited, provided that they are not contained in the guanidine derivative. For example, α- or β-hydroxycarbonic acids, dicarboxylic acids, fatty acids and esters thereof may be blended alone or as a mixture of two or more. Examples of such organic acids include those which are represented by the following formulae (6) to (8) or esters thereof.

$$\begin{array}{c} \text{OH} \\ | \\ \text{XCH—COOH} \end{array} \quad (6)$$

$$R^{10}(CR^{11}OH)_q(CH_2)_r COOH \quad (7)$$

$$\begin{array}{c} (CH_2)_s COOH \\ | \\ (CH_2)_t COOH \end{array} \quad (8)$$

In the above formula (6), X represents a hydrogen atom or $CH_3(C_fH_g)_h$ wherein f is an integer of 1 to 27, g is an integer of 2 to 54 and h is 0 or 1. In formula (7), each of $R^{10}$ and $R^{11}$ represents a hydrogen atom or a saturated or unsaturated, branched, non-branched or cyclic alkyl, aralkyl or aryl group having 1 to 25 carbon atoms, q is an integer of 1 to 9 and r is an integer of 0 to 23. In formula (8), s is an integer of 0 to 9 and t is an integer of 0 to 23.

Illustrative examples of these organic acids include ascorbic acid, ε-aminocaproic acid, erythorbic acid, citric acid, succinic acid, tartaric acid, sorbic acid, dehydroacetic acid, lactic acid, urocanic acid, edetic acid, oxybenzonesulfonic acid, orotic acid, capric acid, glycolic acid, cerotic acid, nicotinic acid, hydroxyethanediphosphonic acid, phytic acid, fumaric acid, malic acid, levulinic acid, acrylic acid and oligomers and polymers thereof.

Illustrative examples of fatty acids include linoleic acid, γ-linolenic acid, columbinic acid, nicosa-(η-6,9,13)-trienic acis, arachidonic acid, α-linolenic acid, thymudonic acid, hexaenic acid, isostearic acid, undecylenic acid, stearic acid, palmitic acid, behenic acid, myristic acid, coconut oil fatty acid, lauric acid, lanolinic acid and DHA, as well as 12-hydroxystearic acid and the like hydroxy-fatty acids, cetylphosphoric acid and the like monoalkylphosphoric acids and dialkylphosphoric acids.

Of these organic and inorganic acids, a dicarboxylic acid represented by the formula (8), particularly succinic acid, is preferred in the present invention because of its excellent skin softening improving effect.

When these organic or inorganic acids are blended in a skin cosmetic preparation, they may be used alone or as a mixture of two or more in an amount of preferably from 0.001 to 30% by weight, more preferably from 0.005 to 20% by weight, most preferably from 0.01 to 10% by weight, including all values and subranges between these several limits in order to improve the skin softening effect. In order to improve the skin softening effect more efficiently, they may be blended with the invention guanidine derivative or salt thereof within the range of, preferably, from 0.5:99.5 to 99.5:0.5, more preferably from 5:95 to 95:5, by weight ratio including all ratios and subranges of ratios between these several limits.

The skin cosmetics of the present invention can be blended further with oil components. Though not particularly limited, examples of such oil components include: hydrocarbons such as solid or liquid paraffin, crystal oil, ceresin, ozokerite, montan wax, squalane, squalene and the like; ester oils such as olive oil, carnauba wax, lanolin, jojoba oil, glycerol monostearic acid ester, glycerol distearic acid ester, glycerol monooleic acid ester, isopropyl stearic acid ester, neopentyl glycol dicaprate, cholesterol isostearate and the like; higher fatty acids such as stearic acid, palmitic acid and the like; higher alcohols such as cetanol, stearyl alcohol and the like; naturally extracted sphingosine derivatives; and synthesized sphingosine derivatives represented by the following formula $$\begin{array}{c} R^{21}-O-CH_2 \\ \phantom{xxxx} | \\ \phantom{xx} O \phantom{xxx} CHOX \\ \phantom{xx} \| \phantom{xxx} | \\ R^{22}-C-N-CH_2 \\ \phantom{xxxx} | \\ \phantom{xxxx} CH_2CH_2OY \end{array}$$

wherein $R^{21}$ represents a straight- or branched-chain saturated or unsaturated alkyl group having 10 to 26 carbon atoms. $R^{22}$ represents a straight- or branched-chain saturated or unsaturated alkyl group having 9 to 25 carbon atoms and each of X and Y represents a hydrogen atom or a sugar residue. These compounds may be used alone or as a mixture of two or more.

These oil compounds may be blended in a skin cosmetic preparation in an amount of preferably from 0.001 to 50% by weight, more preferably from 0.005 to 30% by weight based on total weight including all values and subranges between these several limits.

The skin cosmetics of the present invention can be blended further with sterols which include cholesterol, provitamin $D_3$, campesterol, stegmastanol, stegmasterol, 5-dihydrocholesterol, α-spinasterol, paristerol, cryonasterol, γ-cytosterol, stegmastenol, sargasterol, apenasterol, ergostanol, cytosterol, corbisterol, chondrillasterol, polyferasterol, haliclonasterol, neospongosterol, fucosterol, aptostanol, ergostadienol, ergosterol, 22-dihydroergosterol, brassicasterol, 24-methylenecholesterol, 5-dihydroergosterol, dehydroergosterol, fungisterol, cholestanol, coprostanol, dimosterol, 7-fetocholesterol, latosterol, 22-dehydrocholesterol, β-cytosterol, cholestatrien-3β-ol, coprostanol, cholestanol, ergosterol, 7-dehydrocholesterol, 24-dehydrocholestadion-3β-ol, equilenin, equilin, estrone, 17β-estradiol, androst-4-ene-3β, 17β-diol, dehydroepiandrosterone and the like.

These sterols may be used alone or as a mixture of two or more and blended in a skin cosmetic preparation in an amount of preferably from 0.001 to 50% by weight, more preferably from 0.005 to 30% by weight including all values and subranges between these several limits.

The skin cosmetics of the present invention can be blended further with surface active agents which include for example a polyoxyethylene alkyl ether, a polyoxyethylene fatty acid ester, a polyoxyethylene sorbitan fatty acid ester, a polyoxyethylene sorbitol fatty acid ester, a glycerol fatty acid ester, a polyoxyethylene hardened castor oil alkyl sulfuric ester, a polyoxyethylene alkyl sulfuric ester, an alkyl phosphoric ester, a polyoxyethylene alkyl phosphoric ester, a fatty acid alkali metal salt, a sorbitan fatty acid ester, a glycerine fatty acid ester, an alkyl glyceryl ether and the like.

These surface active agents may be used alone or as a mixture of two or more and blended in a skin cosmetic preparation in an amount of preferably from 0.001 to 50% by weight, more preferably from 0.005 to 30% by weight including all values and subranges between these several limits.

The skin cosmetics of the present invention can also be blended with water soluble polyhydric alcohols comprising two or more hydroxyl groups in a molecule, which include for example ethylene glycol, propylene glycol, 1,3-butylene glycol, 1,4-butylene glycol, dipropylene glycol, glycerol and polyglycerols such as diglycerol, triglycerol, tetraglycerol and the like, glucose, maltose, maltitol, sucrose, fructose, xylitol, sorbitol, maltotriose, threitol, erythritol and higher alcohols prepared by reduction of starch hydrolyzed sugars.

These water soluble polyhydric alcohols may be used alone or as a mixture of two or more and blended in a skin cosmetic preparation in an optionally determined amount depending on the dosage forms, preferably from 0.001 to 75% by weight, more preferably from 0.1 to 25% by weight including all values and subranges between these several limits.

The skin cosmetics of the present invention can also be blended further with powders which include for example extender pigments such as mica, talc, sericite, kaolin, nylon powder, polymethylsill sesquioxane and the like, inorganic pigments such as pearl, organic pigments such as Red No. 202, Red No. 226, Yellow No. 4, aluminium lake and the like and inorganic powder for ultraviolet ray protection use such as of zinc oxide, titanium oxide, zirconium oxide, iron oxide and the like. These powders may be used after silicone treatment with methylhydrogenmethyl polysiloxane, trimethylsiloxy silicate, methylpolysiloxane or the like, fluorine treatment with perfluoroalkyl phosphoric ester, perfluoroalcohol or the like, amino acid treatment with N-acylglutamic acid or the like, lecithin treatment, metal soap treatment, fatty acid treatment or alkyl phosphoric ester treatment.

These powders may be blended in a skin cosmetic preparation in an optionally determined amount depending on the dosage forms, preferably from 0.001 to 50% by weight, more preferably from 0.005 to 30% by weight including all values and subranges between these several limits.

The skin cosmetics of the present invention can also be blended with silicones usually used in cosmetics, which include for example octamethyl polysiloxane, tetradecamethyl polysiloxane, methyl polysiloxane, high polymerization degree methyl polysiloxane and methylphenyl polysiloxane, as well as methyl polycyclosiloxanes such as octamethyl cyclotetrasiloxane, decamethyl cyclopentasiloxane and the like, trimethyl siloxysilicate and denatured silicones such as polyether alkyl denatured silicone, alkyl glyceryl ether denatured silicone and the like.

These silicones may be blended in a skin cosmetic preparation in an optionally determined amount depending on the dosage forms, preferably from 0.001 to 50% by weight, more preferably from 0.005 to 30% by weight including all values and subranges between these several limits.

The skin cosmetics of the present invention can also be blended with various other components which are usually used in cosmetics, quasi drugs, pharmaceutical drugs and the like, within such a range of amount that they do not spoil the object of the present invention. Examples of such components include inorganic salts such as magnesium sulfate, potassium sulfate, sodium sulfate, magnesium chloride, sodium chloride and the like; viscosity adjusting agents such as polyvinyl alcohol, carboxy vinyl polymer, carboxymethyl cellulose, gelatin, tragacanth gum, xanthan gum, hyaluronic acid, tuberose extract, agarose, sodium alginate and the like; antiseptics such as paraben and the like; and pH adjusting agents, wetting agents, UV absorbing agents, pigments, pharmaceutically active components, perfumes and the like.

The skin cosmetics of the present invention may have a pH value of preferably from 2 to 11, more preferably from 3 to 8, including all values and subranges between these several limits in order to maintain normal physiological function of the skin. The skin cosmetics of the present invention can be produced in accordance with conventional means, in desired dosage forms of emulsion type, dispersion type, two-layer type, solubilized type, gel type and the like and in desired preparations such as a facial lotion, a milky lotion, a cream, a pack, a foundation and the like.

The skin cosmetic compositions of the present invention provide excellent softness to the keratin layer continuously and for a prolonged period of time and are effective in providing the skin with a good feeling without stickiness when used. Because of this, skin can be protected from dryness and roughness continuously and safely even in low temperature and/or low humidity conditions or when excess amounts of detergents or solvents are used.

As has been described in the foregoing, novel guanidine derivative (1), (2) or (3) of the present invention and their acid addition salts have a moisturizing function and a keratin softening function and are useful as blending components of skin cosmetics and hair cosmetics. They can also be used as an intermediate material for the production of agricultural chemicals, pharmaceutical drugs and dyestuffs.

Examples of the present invention are given below by way of illustration only and not by way of limitation.

PRODUCTION EXAMPLE 1

2-(2-Hydroxyethoxy)ethylguanidine (1) S-Me isothiourea as a guanidylation reagent To 1.2 liters of distilled water and 150 g (1.43 mol) of 2-(2-aminoethoxy)ethanol in a two-neck pear shaped flask were added 248 g (0.891 mol) of S-Me isothiourea sulfate and 281 g (0.891 mol) of barium hydroxide·$8H_2O$ at room temperature. After 2 days of stirring at room temperature, the thus formed barium sulfate was removed by filtration. The resulting liltrate was concentrated to about ½₀, excess amount of carbon dioxide was bubbled into the thus concentrated liltrate and then about 120 g of crude product was crystallized by adding ethanol. Thereafter, the crude product was recrystallized from 120 ml of distilled water to obtain 73 g of the title compound (white crystals, 0.41 mol, 29% in yield) in the form of ½-carbonate. Results of the analyses of this compound are as follows.

mp: 96°–102° C. (decomposition)

$^1$H-NMR (200 MHz, $D_2O$, TSP standard): δ 3.77 - 3.63 (m, 6 H), 3.41 (t, 2 H, J=5.03 Hz) $^{13}$C-NMR (50 MHz, D20, TSP standard): δ 163.25, 160.15, 74.61, 71.54, 63.20, 44.05

IR (KBr, $cm^{-1}$): 3424, 3200, 3016, 2932, 2904, 2648, 1682, 1642, 1602, 1472, 1460, 1398, 1354, 1256 1224, 1192, 1126, 1062, 1022, 950, 930, 892, 840, 798, 650, 558

(2) Cyanamide as a guanidylation reagent 21.0 g (0.200 mol) of 2-(2-aminoethoxy)ethanol and 11.8 g (0.100 mol) of succinic acid were placed in a 200 ml two neck flask. While heating the flask in a 90° C. oil bath and evaporating water by bubbling nitrogen, 16.8 g (0.200 mol) of 50% aqueous solution of cyanamide was added dropwise spending 3 hours. After 20 hours of additional heating, the product was crystallized from ethanol to obtain 22.8 g of the title compound (white powder, 0.11 mol, 55% in yield) in the form of ½-succinate. Results of the analyses of this compound are as follows.

mp: 104°–114° C. (decomposition)

$^1$H-NMR (200 MHz, $D_2O$, TSP standard): δ 3.76 - 3.61 (m, 6 H), 3.40 (t, 2 H, J=5.04 Hz), 2.40 (s, 2 H)

(3) O-Me isourea as a guanidylation reagent 10.5 g (0.100 mol) of 2-(2-aminoethoxy)ethanol, 50 ml of distilled water and 12.6 g (0.150 mol) of sodium bicarbonate were poured into a 100 ml two neck flask. While keeping the reaction temperature at 15° C. in a water bath, 18.5 g (0.075 mol) of O-Me isourea sulfate was added in small portions spending about 2 hours. Thereafter, the reaction temperature was increased to 20° C., and the reaction was continued for 3 days. After concentration of the reaction solution, the resulting residue was purified by a silica gel column chromatography (eluent, ethanol containing 1% acetic acid) to obtain 7.87 g of the title compound (starch syrup-like, 0.037 mol, 38% in yield) in the form of acetate.

Results of the analysis of this compound are as follows.

$^1$H-NMR (200 MHz, $D_2O$, TSP standard): δ 3.78 - 3.64 (m, 6 H), 3.43 (t, 2 H, J=5.03 Hz), 2.00 (s, 3 H)

(4) Preparation of glutamic acid salt

A 2.34 g (10.0 mmol) portion of an acetic acid salt of the titled compound was dissolved in 50 ml of distilled water in 100 ml pear shaped flask to which was subsequently added 1.47 g (10.0 mmol) of glutamic acid and was heated at 80° C. Water and an acetic acid were distilled away under reduced pressure to obtain 2.90 g of glutamic acid salt of the title compound (starch syrup-like, 9.85 mmol, 98.5% in. yield).

$^1$H-NMR (200 MHz, $D_2O$, TSP standard)t δ 3.78 - 3.64 (m, 7 H), 3.43 (t, 2 H, J=5.03 Hz), 2.35 (t, 2 H, J=7.23 Hz), 2.2-1.9 (m, 2 H)

(5) Preparation of glycolic acid salt

A 2.34 g (10.0 mmol) portion of the above acetic acid salt was dissolved in 20 ml of distilled water in 100 ml pear shaped flask to which was subsequently added 0.760 g (10.0 mmol) of glycolic acid and was heated at 50° C. Water and an acetic acid were distilled away under reduced pressure to obtain 2.18 g of glycolic acid salt of the title compound (starch syrup-like, 9.77 mmol, 97.7% in yield).

$^1$H-NMR (200 MHz, $D_2O$, TSP standard): δ 3.94 (s, 2 H), 3.78 -3.64 (m, 6 H), 3.43 (t, 2 H, J=5.03 Hz)

PRODUCTION EXAMPLE 2

N-b 2-(2-hydroxyethoxy)ethyl-N-methylguanidine

In an atmosphere of nitrogen and at room temperature, to 4.80 g (40.3 mol) of 2-(2-N-methylaminoethoxy)ethanol and 150 ml of distilled water in a 200 ml pear shaped flask were added 20.19 g (72.5 mmol) of S-Me isothiourea sulfate and 22.89 g (72.5 mmol) of barium hydroxide·$8H_2O$. After 2 days of stirring under the same conditions, the thus formed barium sulfate was removed by filtration. The thus obtained filtrate was concentrated and spontaneously cooled, the precipitate thus formed was removed by filtration and then excess amount of carbon dioxide was bubbled into the resulting filtrate. After cooling, the thus formed crystals were collected by filtration and washed to obtain 1.68 g of the title compound (8.74 mmol, 21.7% in yield) in the form of carbonate. Results of the analyses of this compound are as follows.

mp=132.5°–135° C. (decomposition)

$^1$H-NMR (200 MHz, $D_2O$, TSP standard): δ 3.80 - 3.63 (m, 6 H), 3.57 (t, 2 H, J=4.87 Hz), 3.07 (s, 3 H)

$^{13}$C-NMR (50 MHz, $D_2O$, TSP standard): δ 163.04, 160.28, 74.88, 70.52, 63.19, 53.28, 38.77

IR (KBr, $cm^{-1}$): 3408, 3140, 2928, 2900, 2696, 2644, 1700, 1638, 1614, 1466, 1408, 1376, 1352, 1120, 1088, 1076, 1040, 1020, 946, 918, 838

PRODUCTION EXAMPLE 3

2-(2-(2-hydroxyethoxy)ethoxy)ethylguanidine

(1) Preparation of acetic acid salt

To 50 ml of distilled water and 6.06 g (40.6 mol) of 2-(2-(2-hydroxyethoxy)ethoxy)ethanol in a 200 ml pear shaped flask were added 17.0 g (60.9 mmol) of S-Me isothiourea sulfate and 19.2 g (60.9 mmol) of barium hydroxide·$8H_2O$. After 2 days of stirring at room temperature, the thus formed barium sulfate was removed by filtration. Thereafter, the resulting filtrate was concentrated and subjected to purification by a silica gel column chromatography (eluent, ethanol containing 1% acetic acid) to obtain 7.47 g of the title compound (starch syrup-like, 29.7 mmol, 73% in yield) in the form of acetate. Results of the analysis of this compound are as follows.

$^1$H-NMR (200 MHz, $D_2O$, TSP standard): δ 3.78 - 3.63 (m, 10 H), 3.42 (t, 2 H, J=5.01 Hz), 1.96 (s, 3 H)

(2) Preparation of 1/2-succinic acid salt

A 4.67 g (18.6 mmol) portion of the above acetic acid salt was dissolved in 6 ml of ethanol to which was subsequently added 1.10 g (9.3 mmol) of succinic acid. After stirring and subsequent evaporation of the solvent, the resulting residue was dried at 70° C. under a reduced pressure to obtain 4.65 g of the title compound (starch syrup-like, 18.6 mmol, 100% in yield) in the form of ½-succinate. Results of the analyses of this compound are as follows.

$^1$H-NMR (200 MHz, $D_2O$, TSP standard): δ 3.78 - 3.63 (m, 10 H), 3.42 (t, 2 H, J=5.01 Hz), 2.49 (s, 2 H)

$^{13}$C-NMR (50 MHz, $D_2O$, TSP standard): δ 183.85, 160.07, 74.48, 72.48, 72.23, 71.57, 63.13, 44.00, 35.91

IR (KBr, $cm^{-1}$): 3348, 2944, 1678, 1554, 1456, 1394, 1354, 1294, 1248, 1182, 1116, 1068, 930, 850, 810, 710, 650

PRODUCTION EXAMPLE 4

N-(aminoiminomethyl)-trans-4-hydroxy-L-proline:

(1) 135.1 g (1.03 mol) of trans-4-hydroxy-L-proline was dissolved in 200 ml of distilled water in 1l flask by heating at 90° C. 86.6 g (1.03 mol) of 50% aqueous solution of cyanamide was added dropwise spending 2 hours. After 20 hours of additional heating (90° C.), the product was added 250 ml of distilled water and was allowed to stand at room temperature. The precipitate was filtrated and washed to obtain 102 g of the title compound (57% in yield). Results of the analyses of this compound are as follows.

mp: 265° C. (decomposition)

$^1$H-NMR (200 MHz, $D_2O$, TSP standard) δ 4.62-4.45 (m, 1 H), 4.41 (t, 1 H), 3.73 (dd, 1 H), 3.54-3.47 (m, 1 H), 2.53-2.39 (m, 1 H), 2.30-2.17 (m, 1 H)

$^{13}$C-NMR (50 MHz, $D_2O$, TSP standard) δ 179.92, 158.21, 77.71, 63.68, 58.08, 41.51

IR (KBr, $cm^{-1}$): 3520, 3396, 3220, 3116, 2964, 2892, 2768, 1690, 1618, 1550, 1480, 1444, 1396, 1354, 1326, 1306, 1244, 1224, 1186, 1158, 1100, 1082, 1054, 990, 974, 838, 800, 748, 732, 690, 596, 566, 482, 442

(2) 2.62 g (20.0 mmol) of trans-4-hydroxy-L-proline and 12 ml of distilled water were placed in 25 ml flask followed by stirring at room temperature to dissolve trans-4-hydroxyproline. While soaking the flask in a 15° C. thermostat to keep the reaction temperature at 15° C., 1.20 g (30.0 mmol) of sodium hydroxide was added to the mixture and then 3.69 g (15 mmol) of O-Me isourea sulfate was added in small portions. Thereafter, 10 ml of distilled water was added to the mixture and the reaction temperature was increased to 20° C., and the reaction was continued for 3 days. The reaction solution was concentrated at 60° C. under reduced pressure and was cooled to stand at room temperature. The precipitate was filtered and washed to obtain 2.03 g of the title compound (59% in yield).

(3) 100 g (763 mmol) of trans-4-hydroxy-L-proline and 500 g of distilled water were placed in 1l flask and were stirred at room temperature to dissolve trans-4-hydroxyproline. Thereafter, 167 g (600 mmol) of S-Me isourea sulfate and 189 g (600 mmol) of Ba(OH)$_2$·$8H_2O$ were added to the mixture in small portions to be respective equivalent. After the completion of the addition, the reaction was continued for 24 hours at room temperature. The thus formed barium sulfate was removed by filtration and the thus obtained liltrate was concentrated and was added ethanol. The precipitate thus formed was filtrated and washed to obtain 105 g of the title compound (61% in yield).

PRODUCTION EXAMPLE 5

N-3-methoxypropyl-N-ethylguanidine 3.00 g (25.6 mmol) of N-ethyl-3-methoxypropylamine and 1.54 g (25.6 mmol) of acetic acid were placed in a 50 ml two neck flask. While heating the flask in a 90° C. oil bath, 1.08 g (25.6 mmol) of cyanamide was added. After 12 hours of the reaction, the product was purified by a silica gel column chromatography (eluent, chloroform/ethanol=½ containing 0.5% acetic acid) to obtain 2.80 g of the title compound (wax-like, 12.8 mmol, 50.0% in yield) in the form of acetate. Results of the analysis of this compound are as follows.

$^1$H-NMR (200 MHz, $D_2O$, TSP standard): δ 3.50 (t, 2 H, J=5.93 Hz), 3.45 - 3.32 (m, 4 H), 3.35 (s, 3 H), 2.01 (s, 3 H), 2.00 - 1.64 (m, 2 H)

$^{13}$C-NMR (50 MHz, $D_2O$, TSP standard) δ: 180.50, 158.52, 71.35, 60.50, 47.54, 46.05, 29.23, 24.35, 14.28

IR (KBr, $cm^{-1}$): 3352, 2984, 1690, 1580

PRODUCTION EXAMPLE 6

N-5-hydroxypentyl-N-methylguanidine 5.91 g (50.4 mmol) of 5-N-methylamino-1-pentanol and 3.10 g (51.6 mmol) of acetic acid were placed in a 50 ml two neck flask. While heating the flask in a 90° C. oil bath, 3.11 g (74.0 mmol) of cyanamide Was added. After 6 hours of the reaction, the product was purified by a silica gel column chromatography (eluent, chloroform/ethanol=½ containing 0.5% acetic acid) to obtain 8.70 g of the title compound (wax-like, 39.7 mmol, 78.7% in yield) in the form of acetate. Results of the analysis of this compound are as follows.

$^1$H-NMR (200 MHz, $D_2O$, TSP standard): δ 3.61 (t, 2 H, J=6.43 Hz), 3.34 (t, 2 H, J=7.38 Hz), 3.02 (s, 3 H), 1.98 (s, 3 H), 1.80 - 1.54 (m, 4 H), 1.42 - 1.30 (m, 2 H)

$^{13}$C-NMR (50 MHz, $D_2O$, TSP standard) δ: 181.70, 158.99, 64.16, 52.96, 38.43, 33.61, 28.89, 24.90

IR (KBr, $cm^{-1}$): 3232, 2940, 2864, 1690, 1622, 1576, 1478, 1414, 1340, 1128, 1092, 692, 650

PRODUCTION EXAMPLE 7

2-(2-methoxyethoxy)ethylguanidine 5.96 g (50.0 mmol) of 2-(2-methoxyethoxy)ethylamine and 3.00 g (50.0 mmol) of acetic acid were placed in a 30 ml two neck flask. While heating the flask in a 90° C. oil bath, 3.10 g (73.7 mmol) of cyanamide was added. After 5 hours of the reaction, the product was purified by a silica gel column chromatography (eluent, chloroform/ethanol=2/1 containing 0.5% acetic acid) to obtain 3.15 g of the title compound (wax-like, 14.2 mmol, 28.5% in yield) in the form of acetate. Results of the analysis of this compound are as follows.

$^1$H-NMR (200 MHz, $D_2O$, TSP standard): δ 3.8 - 3.6 (m, 6 H), 3.45 - 3.30 (m, 5 H), 1.92 (s, 3 H)

$^{13}$C-NMR (50 MHz, $D_2O$, TSP standard) δ: 183.70, 160.06, 73.72, 72.24, 71.54, 60.77, 43.92, 26.06

IR (KBr, $cm^{-1}$): 3348, 3104, 3084, 1686, 1650, 1554, 1456, 1406, 1356, 1304, 1246, 1202, 1100, 1018, 920, 846, 800, 760, 648

PRODUCTION EXAMPLE 8

N-2-hydroxypropyl-N-methylguanidine 2.23 g (25.0 mmol) of 1-N-methylamino-DL-2-propanol and 1.58 g (26.3 mmol) of acetic acid were placed in a 20 ml two neck flask. While heating the flask in a 90° C. oil bath, 2.30 g (54.7 mmol) of cyanamide was added. After 6 hours of the reaction, the product was purified by a silica gel column chromatography (eluent, chloroform/ethanol=2/1 containing 0.5% acetic acid) to obtain 1.92 g of the title compound (wax-like, 10.0 mmol, 40.2% in yield) in the form of acetate. Results of the analysis of this compound are as follows.

$^1$H-NMR (200 MHz, $D_2O$, TSP standard): δ 4.25 - 4.12 (m, 1 H), 3.42 (d, 2 H, J=5.92 Hz), 3.14 (s, 3 H), 2.03 (s, 3 H), 1.27 (d, 3 H, J=6.39 Hz)

$^{13}$C-NMR (50 MHz, $D_2O$, TSP standard) δ: 181.81, 160.24, 67.90, 60.06, 39.53, 24.85, 22.04

IR (KBr, $cm^{-1}$): 3328, 3044, 1682, 1624, 1576, 1414, 1338, 1134, 1070, 1038, 684, 650

PRODUCTION EXAMPLE 9

N,N-bis-(2-(2-methoxyethoxy)ethyl)guanidine 1.54 g (6.98 mmol) of di-2-(2-methoxyethoxy)ethylamine and 0.423 g (7.04 mmol) of acetic acid were placed in a 20 ml two neck flask. While heating the flask in a 90° C. oil bath, 0.630 g (15.0 mmol) of cyanamide was added. After 6 hours of the reaction, the product was purified by a silica gel column chromatography (eluent, chloroform/ethanol=2/1 containing 0.5% acetic acid) to obtain 2.07 g of the title compound (starch syrup-like, 6.40 mmol, 91.7% in yield) in the form of acetate. Results of the analysis of this compound are as follows.

$^1$H-NMR (200 MHz, $D_2O$, TSP standard): δ 3.79 - 3.69 (m, 8 H), 3.65 - 3.58 (m, 8 H), 3.38 (s, 6 H), 1.92 (s, 3 H)

$^{13}$C-NMR (50 MHz, $D_2O$, TSP standard) δ: 183.70, 161.08, 73.66, 72.52, 70.70, 60.73, 51.77, 26.06

IR (KBr, $cm^{-1}$): 3232, 2984, 2904, 2824, 1694, 1580, 1516, 1470, 1414, 1348, 1200, 1126, 1076, 1008, 844, 682

PRODUCTION EXAMPLE 10

2-(2-guanidinoethoxy)ethyl benzoate 2.14 g (10.2 mmol) of 2-(2-aminoethoxy)ethyl benzoate and 0.624 g (10.4 mmol) of acetic acid were placed in a 50 ml two neck flask. While heating the flask in a 90° C. oil bath, 0.680 g (16.2 mmol) of cyanamide was added. After 6 hours of the reaction, the product was purified by a silica gel column chromatography (eluent, chloroform/ethanol=½ containing 0.5% acetic acid) to obtain 1.97 g of the title compound (wax-like, 6.33 mmol, 62.0% in yield) in the form of acetate. Results of the analysis of this compound are as follows.

$^1$H-NMR (200 MHz, $D_2O$, TSP standard): δ 8.07 (d, 2 H, J=7.53 Hz), 7.72 (t, 1 H, J=7.33 Hz), 7.57 (t, 2 H, J=7.62), 4.54 (t, 2 H, J=4.38 Hz), 3.94 (t, 2 H, J=4.40 Hz), 3.77 (t, 2 H, J=4.92 Hz), 3.40 (t, 2 H, J=4.91 Hz), 1.93 (s, 3 H)

$^{13}$C-NMR (50 MHz, $D_2O$, TSP standard) δ: 183.74, 170.72, 160.00, 136.43, 132.05, 131.72, 131.31, 71.84, 71.31, 66.92, 43.95, 26.09

IR (KBr, $cm^{-1}$): 3352, 3068, 1724, 1680, 1606, 1558, 1456, 1406, 1316, 1278, 1110, 1070, 710, 648

PRODUCTION EXAMPLE 11

2-(2-guanidinoethoxy)ethyl acetate 2.06 g (9.99 mmol) of 2-(2-hydroxyethoxy) ethylguanidine succinate, 8 ml of triethylamine, 0.122 mg (1.0 mmol) of 4-N,N-dimethylaminopyridine and 1.02 g (9.99 mmol) of acetic anhydride were placed in a 50 ml two neck flask and were stirred for 1 hour at room temperature. After the upper phase was removed by decantation, the obtained crude product was washed five times with 50 ml of diethylether. The product was purified by a silica gel column chromatography (eluent, chloroform/ethanol=2/1 containing 0.5% acetic acid) to obtain 1.00 g of the title compound (starch syrup-like, 4.0 mmol, 40.0% in yield) in the form of acetate. Results of the analysis of this compound are as follows.

$^1$H-NMR (200 MHz, D$_2$O, TSP standard): δ 4.26 (t, 2 H, J=4.47 Hz), 3.78 (t, 2 H, J=4.47 Hz), 3.70 (t, 2 H, J=4.98 Hz), 3.40 (t, 2 H, J=4.95 Hz), 2.12 (s, 3 H), 1.99 (s, 3 H)

$^{13}$C-NMR (50 MHz, D$_2$O, TSP standard) δ: 181.82, 177.00, 160.21, 71.78, 71.39, 66.66, 44.04, 24.83, 23.13

IR (KBr, cm$^{-1}$): 3372, 1740, 1676, 1554, 1408, 1250, 1134, 1052, 1014, 648

In the following examples, the following compounds 1 to 4 of formula (1) (compound 1) or (2) (compounds 2–4) were used as guanidine derivatives or salts thereof, with their respective formula symbols shown in Table 1. Of these, compound 1 is the one obtained in the above Production Example 1(1).

TABLE 1

| Compound No. | R$^1$ | A | m | B | n | D | E | l | G |
|---|---|---|---|---|---|---|---|---|---|
| Compound 1 | H | C$_2$H$_4$ | 2 | — | — | — | H | — | — |
| Compound 2 | H | — | — | — | — | — | — | 5 | —OH |
| Compound 3 | H | — | — | — | — | — | — | 2 | —COOH |
| Compound 4 | H | — | — | — | — | — | — | 2 | —PO$_4$H$_2$ |

EXAMPLES 1 TO 4 AND COMPARATIVE EXAMPLE 1

Skin cosmetics having the respective compositions shown in Table 2 were produced in a conventional manner. Keratin layer-softening effects of the thus produced skin cosmetics were examined by the following test method, with the results also shown in Table 2.

(Test Method)

A piece of the keratin layer having a size of 30×5 mm was soaked in each of the cosmetic preparations for 3 hours. After drying, the test piece was allowed to stand in an atmosphere of constant humidity and then checked for its tan δ value using a dynamic elastic viscosity measuring apparatus (manufactured by Rheology). The results are expressed as relative values when the value of Comparative Example 1 is defined as tan δ=1. Higher values indicate greater softening effects.

TABLE 2

| Components (% by weight) | Examples | | | | Comp.Ex. |
|---|---|---|---|---|---|
| | 1 | 2 | 3 | 4 | 1 |
| Compound 1 | 2.5 | — | — | — | — |
| Compound 2 | — | 1.0 | — | — | — |
| Compound 3 | — | — | 5.0 | — | — |
| Compound 4 | — | — | — | 5.0 | — |
| Arginine | — | — | — | — | 5.0 |
| Succinic acid | 2.0 | 1.0 | 5.0 | 5.0 | 5.0 |
| Purified water | 95.5 | 98.0 | 90.0 | 90.0 | 90.0 |
| pH | 6.0 | 6.0 | 6.0 | 6.0 | 6.0 |
| Softening effect (tan δ) | 1.48 | 1.38 | 1.10 | 1.33 | 1 |

EXAMPLE 5

A cream (pH=6.0) of the following formulation was produced in a conventional manner.

| (Components) | (% by weight) |
|---|---|
| stearic acid | 2.0 |
| squalane | 2.0 |
| cholesterol | 3.0 |
| olive oil | 1.0 |
| cetanol | 7.0 |
| jojoba oil | 2.0 |
| arginine 2-hexadecyl phosphate | 2.0 |
| polyoxyethylene (40 EO) hardened castor oil | 0.5 |
| glycerol | 10.0 |
| 1,3-butylene glycol | 5.0 |
| compound 1 | 2.0 |
| compound 3 | 1.0 |
| succinic acid | 1.0 |
| purified water | balance |
| total | 100.0 |

When the cream of the above formulation was subjected to organoleptic examination by expert panelists, it showed excellent skin softening effect and was good in feeling to the skin with no stickiness when used.

EXAMPLE 6

A milky lotion (pH=6.0) of the following formulation was produced in a conventional manner.

| (Components) | (% by weight) |
|---|---|
| palmitic acid | 0.5 |
| olive oil | 2.0 |
| cetanol | 1.0 |
| jojoba oil | 5.0 |
| sodium monohexadecyl phosphate | 2.0 |
| sorbitan monostearate | 0.5 |
| glycerol | 15.0 |
| ethanol | 5.0 |
| compound 4 | 4.0 |
| compound 2 | 2.0 |
| lactic acid | 2.0 |
| purified water | balance |
| total | 100.0 |

When the milky lotion of the above formulation was subjected to organoleptic examination by expert panelists, it showed excellent skin softening effects and has a good feeling to the skin with no stickiness when used.

EXAMPLE 7

A facial lotion (pH=6.0) of the following formulation was produced in a conventional manner.

| (Components) | (% by weight) |
|---|---|
| compound 1 | 7.0 |
| compound 4 | 5.0 |
| citric acid | 1.0 |
| 86% glycerol | 15.0 |
| polyethylene glycol (PEG 1500, manufactured by Sanyo Chemical Industries) | 2.0 |
| hyaluronic acid | 0.05 |
| dipropylene glycol | 5.0 |

| (Components) | (% by weight) |
|---|---|
| purified water | balance |
| total | 100.0 |

When the facial lotion of the above formulation was subjected to organoleptic examination by expert panelists, it showed excellent skin softening effects and had a good feeling to the skin with no stickiness when used.

EXAMPLE 8

A pack (pH=6.0) of the following formulation was produced in a conventional manner.

| (Components) | (% by weight) |
|---|---|
| polyvinyl alcohol (Gosenol EG-30, manufactured by The Nippon Synthetic Chemical Industry) | 11.7 |
| 1,3-butylene glycol | 2.5 |
| glycerol | 1.0 |
| titanium oxide | 1.5 |
| compound 3 | 10.0 |
| compound 4 | 5.0 |
| tartaric acid | 7.0 |
| purified water | balance |
| total | 100.0 |

When the pack of the above formulation was subjected to organoleptic examination by expert panelists, it showed excellent skin softening effects and had a good feeling to the skin with no stickiness when used.

EXAMPLE 9

A gel (pH=6.0) of the following formulation was produced in a conventional manner.

| (Components) | (% by weight) |
|---|---|
| polyacrylic acid (Carbopol, manufactured by Goodrich) | 0.5 |
| potassium hydroxide | 0.15 |
| Glucum | 10.0 |
| 86% glycerol | 10.0 |
| glycine betaine | 3.0 |
| N-(aminoiminomethyl)-trans-4-hydroxy-proline | 1.5 |
| succinic acid | 1.5 |
| purified water | balance |
| total | 100.0 |

When the gel of the above formulation was subjected to organoleptic examination by expert panelists, it showed excellent skin softening effects and had a good feeling to the skin with no stickiness when used.

EXAMPLE 10

A facial lotion (pH=6.0) of the following formulation was produced in a conventional manner.

| (Components) | (% by weight) |
|---|---|
| compound 1 | 3.0 |
| compound 3 | 4.0 |
| 86% glycerol | 15.0 |
| dipropylene glycol | 5.0 |
| purified water | balance |
| total | 100.0 |

When the facial lotion of the above formulation was subjected to organoleptic examination by expert panelists, it showed excellent skin softening effects and had a good feeling to the skin with no stickiness when used.

While the invention has been described in detail and with reference to specific embodiments thereof, it will be apparent to one skilled in the art that various changes and modifications can be made therein without departing from the spirit and scope thereof.

This application is based on Japanese patent application No. Hei. 6-173043 filed Jul. 26, 1994, incorporated herein by reference.

What is claimed is:

1. A skin cosmetic preparation, comprising:

0.001 to 50% by weight, based on total weight, of a guanidine derivative, and 0.001 to 30%, based on total weight, of an organic acid or ester thereof, wherein said guanidine derivative is represented by the following formula (1), (2), (3) or an acid addition salt thereof:

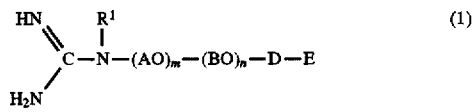

(1)

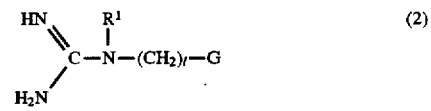

(2)

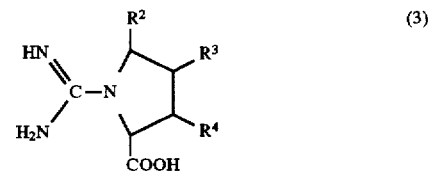

(3)

wherein in formula (1) A and B may be the same or different from each other and each represents an alkylene group having 2 to 8 carbon atoms, D represents a single bond, —CO— or an alkylene group having 1 to 6 carbon atoms, E represents a hydrogen atom, a lower alkyl group, an aralkyl group having 7 to 12 carbon atoms, a phenyl group or a naphthyl group, said aralkyl, phenyl and naphthyl group being unsubstituted or substituted by an amino group which may be substituted with a lower alkyl group; nitro; cyano; hydroxyl: a carboxylic acid residue which may form an ester with a lower alkyl group, a lower alkyl halide or an aralkyl group having 7–12 carbon atoms; carbamoyl a halogen atom; a lower alkyl group; or a lower alkoxy group, m is an integer of 1 to 6, n is an integer of 0 to 6 and $R^1$ represents a hydrogen atom, a lower alkyl group or —(AO)$_m$—(BO)$_n$—D—E, with the proviso that —(AO)$_m$—(BO)$_n$—D—E is not a hydroxyethyl group when $R^1$ is methyl group;

in formula (2), l is an integer of 1 to 10, G represents a hydrogen atom, a hydroxyl group, a carboxyl group, a sulfonic acid group or a phosphoric acid group and $R^1$ is as defined above, and;

in formula (3), one of $R^2$, $R^3$ and $R^4$ is a hydroxyl group and others are hydrogen atoms.

2. The skin cosmetic preparation according to claim 1 wherein said organic acid is a dicarboxylic acid.

3. A method for softening the keratin layer which comprises applicating to the skin an effective amount of the guanidine derivative or an acid addition salt thereof as claimed in claim 1.

4. A method of preparing the skin cosmetic preparation of claim 1, comprising:

mixing said guanidine derivative and said organic acid or ester thereof.

* * * * *

UNITED STATES PATENT AND TRADEMARK OFFICE
CERTIFICATE OF CORRECTION

PATENT NO. : 5,723,133
DATED : March 3, 1998
INVENTOR(S) : Minoru NAGAI et al.

It is certified that error appears in the above-identified patent and that said Letters Patent is hereby corrected as shown below:

On the title page, in Item [30], the third Foreign Application Priority Data has been left out. It should read:

--Oct. 13, 1994 [JP] Japan.................6-247450--

Signed and Sealed this

Twenty-eighth Day of April, 1998

Attest:

BRUCE LEHMAN

Attesting Officer

Commissioner of Patents and Trademarks